United States Patent [19]

Masson

[11] Patent Number: 5,551,312

[45] Date of Patent: Sep. 3, 1996

[54] DEVICE FOR SAMPLING AND PUMPING LIQUIDS CONTAINED IN A CHEMICAL REACTION VESSEL, DRUM OR STORAGE TANK

[76] Inventor: Guy Masson, 5041 Park Forest Dr., Baton Rouge, La. 70816

[21] Appl. No.: 401,989

[22] Filed: Mar. 10, 1995

Related U.S. Application Data

[63] Continuation-in-part of Ser. No. 196,127, Feb. 17, 1994, Pat. No. 5,450,763.

[51] Int. Cl.[6] .................................................. G01N 1/14
[52] U.S. Cl. ............................ 73/863.810; 73/863.830; 73/864.730; 73/864.310
[58] Field of Search ......................... 73/863.83, 864.84, 73/863.81, 864.34, 864.73, 864.74, 864.62, 864.11, 864.13, 864.35

[56] References Cited

U.S. PATENT DOCUMENTS

| | | | |
|---|---|---|---|
| 2,158,803 | 5/1939 | Renfro | 73/863.83 |
| 2,426,369 | 8/1947 | Paulsen | 73/863.83 |
| 3,039,309 | 6/1962 | Vesper et al. | 73/863.83 |
| 3,813,945 | 6/1974 | Crumal | 73/864.31 |
| 4,196,627 | 4/1980 | Locher | 73/864.73 |
| 4,198,862 | 4/1980 | Rubin | 73/863.83 |
| 4,262,533 | 4/1981 | Jaeger | 73/863.83 |
| 5,029,484 | 7/1991 | Somers et al. | 73/863.83 |

FOREIGN PATENT DOCUMENTS

1770808 10/1992 U.S.S.R. .............. 73/864.73

*Primary Examiner*—Hezron E. Williams
*Assistant Examiner*—Nashmiya Ashraf
*Attorney, Agent, or Firm*—Silverman, Cass & Singer, Ltd.

[57] ABSTRACT

A device for sampling and pumping liquids contained in a chemical reaction vessel, drum, or storage tank. A conduit is submerged in a liquid and linked to a cylinder having a piston connected by means of a semi-rigid wire to a manually-operated lever or automatic control system. At the beginning of the cycle, the piston is positioned outside of its associated cylinder, leaving sufficient space for the liquid to enter. When the piston is drawn into the cylinder, the liquid is pushed into the desired sampling container or to a chamber that contains a sensor which continuously measures the parameters of the liquid, when the system is operating cyclically.

12 Claims, 3 Drawing Sheets

DEVICE FOR SAMPLING AND PUMPING LIQUIDS CONTAINED IN A CHEMICAL REACTION VESSEL, DRUM OR STORAGE TANK

CROSS-REFERENCE TO RELATED APPLICATION

This application is a continuation-in-part of U.S. application Ser. No. 08/196,127, filed Feb. 17, 1994, now U.S. Pat. No. 5,450,763, issued Sep. 19, 1995.

BACKGROUND OF THE INVENTION

1. Field of the Invention

The present invention relates to a device for sampling and pumping liquids contained in a chemical reaction vessel, drum, or storage tank.

2. Description of the Related Art

A particular application of the device of the present invention is in chemical or nuclear industry plants in which it is advisable, particularly during manufacturing processes, to continuously analyze or take samples of liquids that are often noxious, with which the operator should not come into contact, and whose very fumes may be dangerous.

Previously known devices generally include apparatus equipped with conduits for taking samples of liquids using suction systems or suction pumps. However, it is sometimes impossible to use such a sampling device when a reactor is operating under vacuum conditions or when the vapor pressure of the liquid is high. Such a device works well when the liquid in question is under a high vapor pressure.

Another known device is satisfactory but requires several valves, a pressure-fed nitrogen supply, a large pipe network, and a considerable number of components of various types. This sophisticated system requires that it be washed, rinsed with a solvent, and dried by injection of pressure-fed nitrogen after each sampling operation; it is then necessary to eliminate large quantities of contaminated solvent by regeneration or combustion, sometimes at high temperatures, and to clean with a saturated solvent gas, all of which leads to an appreciable increase in pollution of the environment. In addition, the use of a pressure-fed gas presents a potential risk for the operator, primarily due to the possibility of having components or seals burst.

The device disclosed in applicant's cross-referenced related application discloses another device in which the liquid to be sampled is removed from a vessel by a cup which is withdrawn in a closed environment.

SUMMARY OF THE INVENTION

The present invention concerns an improved sampling device which operates according to the following principle: a conduit is placed in a reactor with, at its lower extremity, a cylinder in which a piston is connected to an operating lever by means of a semi-rigid wire. At the beginning of the cycle, the piston is far enough removed from the cylinder to allow the liquid to enter into the cylinder. When the piston is drawn in, its seal fits into a flared mouth of the cylinder, sealing it, and slides up the internal walls of the cylinder without leaking. As the piston is drawn in, it pushes the liquid contained in the cylinder through the conduit. The liquid then flows by means of gravity into an inclined tube located outside of the reactor. The withdrawal of tapered stoppers from the inclined tube and container opens up a passage which allows the liquid to flow in the desired direction, that is, into a sampling receptacle.

A chamber located in the return conduit to the reactor contains a measurement sensor that is submerged into the liquid. The sensor can continuously analyze the parameters (i.e.: pH) of the liquid and send measured values to a remote indicator. The surplus liquid feeding into the chamber overflows and returns to the reactor. A small hole in the bottom of the chamber allows it to be completely drained.

The liquid continues to circulate through the system for as long as the piston is operating. Thus, the system operates like a piston-type positive displacement pump. The design of the pump is unique in that it does not include a blocking valve, either at admission or discharge; such valves are required on all positive displacement pumps.

The invention presents numerous advantages, the most important one being that it permits liquid sampling under all circumstances, regardless of the pressure and temperature conditions inside the reactor, and without modifying these conditions; i.e., sampling may take place when the liquid in the reactor is under high vacuum conditions, even below an absolute pressure of one millimeter of a water column, and also when the liquid in question has a high vapor pressure. Importantly, in the present invention the pumped liquid is never subjected to a pressure lower than that of its surrounding environment; that is, contrary to known pumps, the liquid is always pushed and never suctioned.

An important advantage of the system of the present invention is that the sampling is directly representative, thereby eliminating the need for any pre-extraction, a process which sometimes presents real problems of elimination and environmental pollution. Another significant advantage resides in the fact that the liquid circulates in conduits containing no obstructions, no blockage and control units or cavities in which the liquid can stagnate, thereby allowing sampling of viscous liquids or liquids containing suspended matter. The entire system is designed to drain completely in a very short time, thereby solving problems related to substances subject to crystallization. As for liquids which have a tendency to stick to internal walls of conduits, it is interesting to note that operating the device continuously or just before sampling without actually taking a sample, accomplishes the function of rinsing it with the liquid itself; this avoids the need for cleaning solvents which are mixed into toxic substances which must be regenerated or burned, thereby causing pollution of the environment. The system is positioned on the upper, unwetted part of the storage tank, and thus addresses an important safety issue by avoiding the installation of another sampling device sideways toward the bottom, a potentially dangerous position due to the risk of seal rupture or device malfunction, if which should occur, would leave the operator no recourse but to watch helplessly as the tank leaked itself dry.

The system of the present invention provides a safe, simple method for sampling and pumping highly toxic liquids contained in a reactor, drum, or storage tank, without requiring contact with the liquids, without polluting the environment and without endangering human operators.

BRIEF DESCRIPTION OF THE DRAWINGS

The drawings schematically illustrate the embodiments of the invention.

DESCRIPTION OF THE PREFERRED EMBODIMENTS

Figure 1:
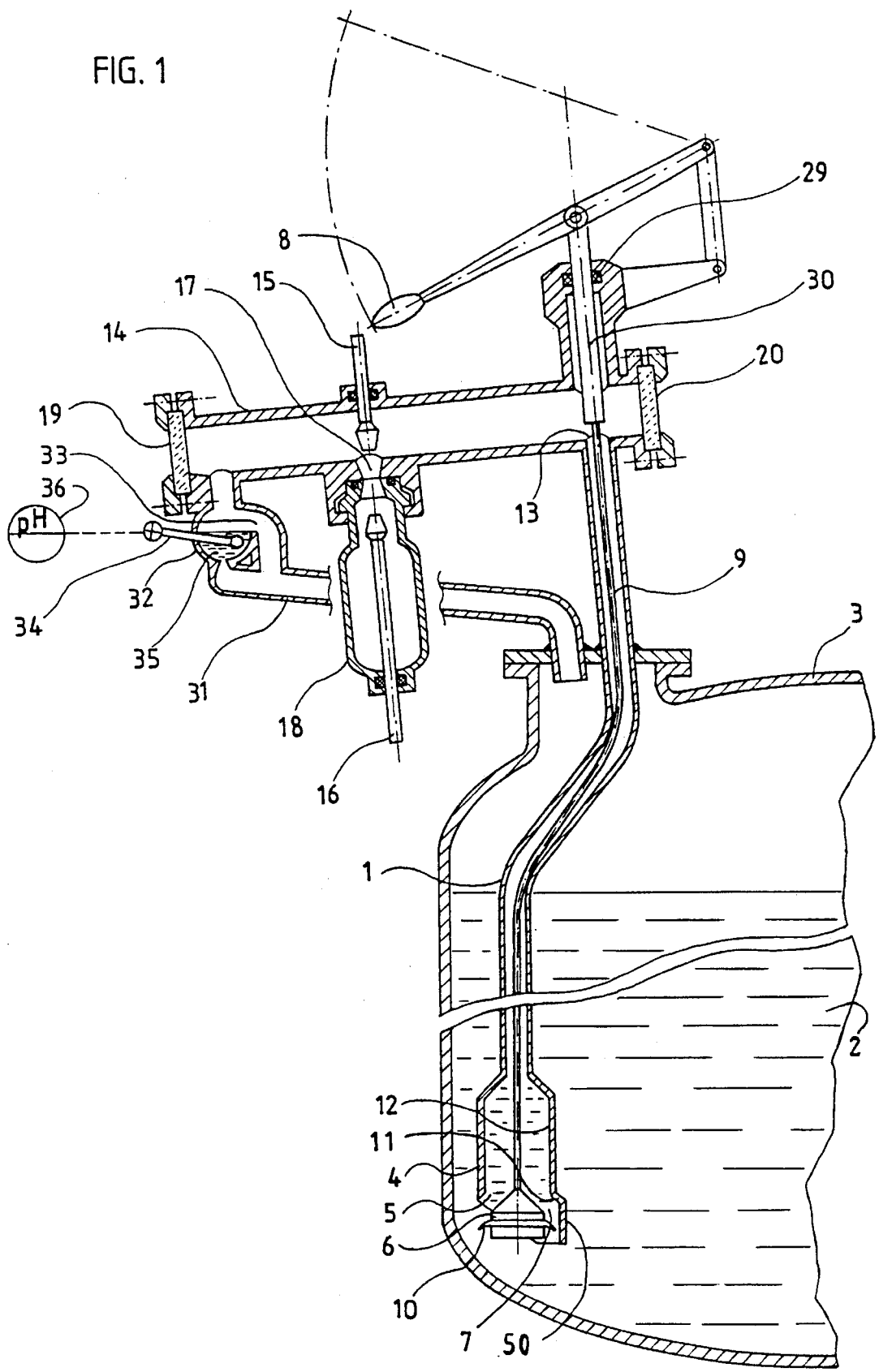
FIG. 1 is cross-sectional view of the device of the invention using a manual control lever, showing the piston outside of the cylinder.
Figure 2:
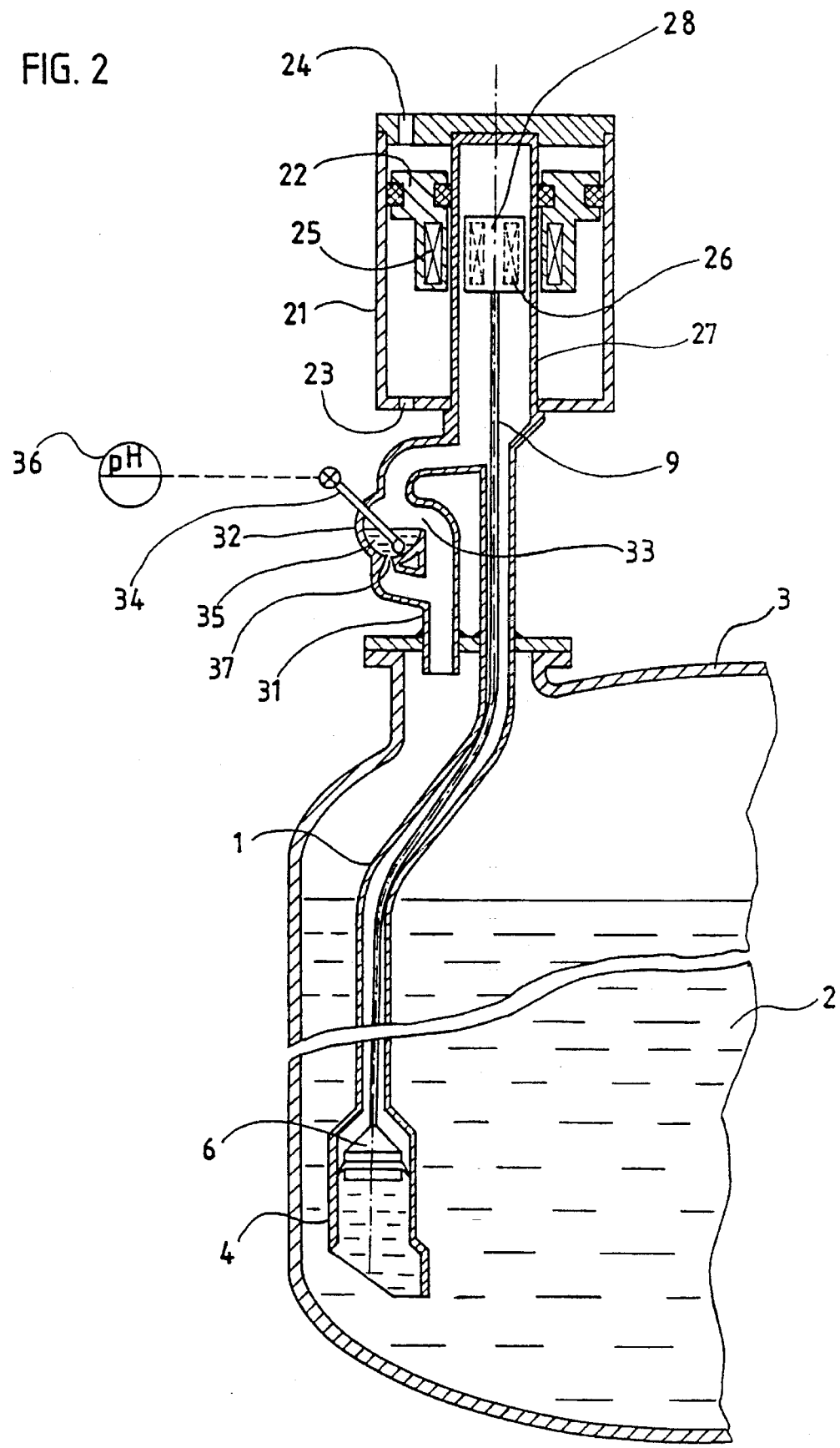
FIG. 2 is a cross-sectional view of the device of the invention using a pneumatic jack control, showing the piston drawn into the cylinder.

Referring to FIGS. 1 and 2, a conduit 1 is submerged in liquid 2 of reactor 3. The end of conduit 1 is connected to cylinder 4 in which piston 6 is engaged in opening 5. Space 7 between the edge of cylinder 4 and piston 6, when the piston is in the fully extended position, allows the liquid to enter the cylinder.

Semi-rigid wire 9 slides through the conduit, and connects piston 6 to control lever 8. Operation of lever 8 draws in piston 6; an o-ring seal with elastic lip 10 fits into and seals the passage formed by the flared extremity 11 of the cylinder and then slides up the internal walls 12 of the cylinder without leakage. Piston 6, pulled by lever 8, pushes the liquid contained inside cylinder 4 up through conduit 1 and out through opening 13; then the liquid flows by gravity into inclined tube 14. Sampling can now take place.

In order to sample, all that is needed is to pull out tapered stoppers 15 and 16 in such a way as to open intersecting passage 17 and allow the liquid to flow into sampling container 18. The flow of liquid within inclined tube 14 can be visually monitored through the sight glass 19; any required lighting is provided by an electric light, not shown, located outside of the sight glass 20. A few repeated movements of lever 8 are all that is necessary to obtain the required quantity of liquid; when the liquid stops flowing into passage 17, as seen from sight glass 19, the container 18 is full and the liquid surplus is returned to the reactor via return conduit 31.

FIG. 2 illustrates a cross-section of an automatic control system operated with pneumatic jack 21 whose piston 22 is moved in one direction or the other by introducing compressed air alternately through opening 23 and opening 24. Inside pneumatic piston 22 there is a permanent ring magnet 25 which pulls another permanent ring magnet 26 up cylinder wall 27. The second magnet 26 is molded inside plastic cylindrical holder 28 to resist corrosion and is connected to pumping piston 6 by means of semi-rigid wire 9. This magnet pulling system has the advantage of using only static seals, not shown in the drawing, with the result that the seals are not subject to wear and tear through shaft movement and, therefore, leaks are very rare in comparison with the use of dynamic seal 29 mounted on rod 30 of control lever 8 shown in FIG. 1. Liquid retention compartment 32 fits in return conduit 31 and contains an overflow section 33 and measurement sensor 34, submerged in liquid 35. There is a small hole 37 in the bottom of compartment 32 whose purpose is to keep the compartment filled to overflow level into overflow section 33, as long as liquid is being supplied to the compartment, and to allow the compartment to drain completely, once it is no longer being supplied with liquid. Measurement sensor 34 in compartment 32 makes it possible to continuously measure the parameters of the liquid, and the measured value can be read on remote indicator 36; for example, compartment 32 is often used to measure pH. Continuous measurement requires that the control system of pumping piston 6 function continuously, for example, through use of pneumatic jack 21 shown in FIG. 2. This figure also shows an extension 50 of cylinder 4, the purpose of which is to protect the piston 6 against turbulence of the liquid when the piston is in its extended position outside the cylinder.

Figure 3:
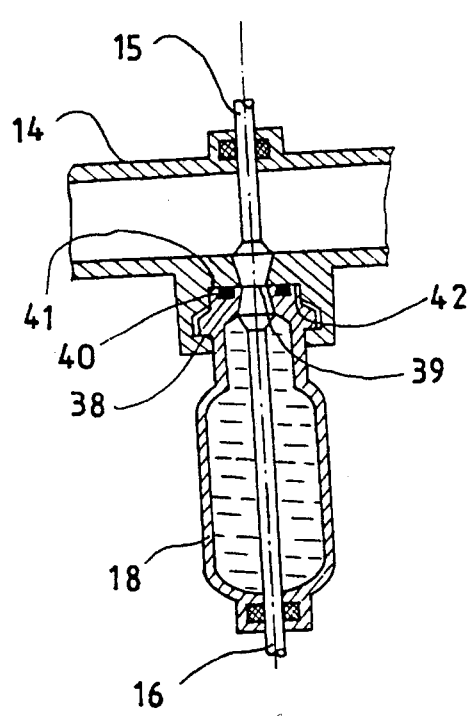
FIG. 3 is an enlarged cross-sectional view showing the container closed and ready to be disconnected.

FIG. 3 is an enlarged view of container 18, shown connected to the inclined tube 14 by means of bayonet coupling 38 before being disconnected. This figure demonstrates that there is no dead volume at point 39 between stem stopper 15 and stem stopper 16. This is made possible through the use of elastic embedded seal 40 which compresses until face 41 of the container opening comes into contact with face 42 of inclined tube opening 14. The absence of dead space ensures that there is no leakage of substance into the atmosphere when the container is disconnected.

Figure 4:
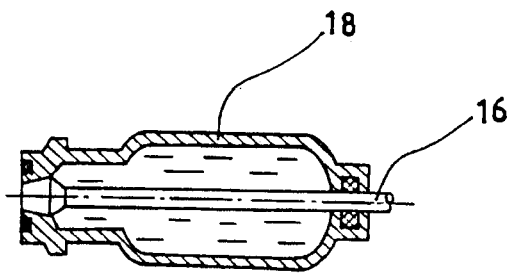
FIG. 4 is a cross-sectional view of a liquid-filled container, closed and disconnected during transport such as to an analysis laboratory.

FIG. 4 shows container 18 full of liquid and disconnected from the system. With stem stopper 16 in closed position, this container of toxic liquid meets all required safety standards for transport to an analysis laboratory.

Figure 5:
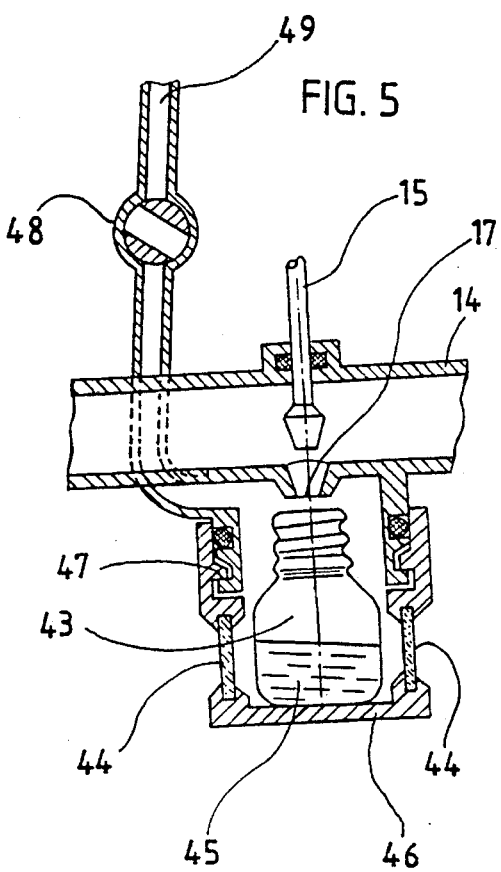
FIG. 5 is a cross-sectional view showing the use of a bottle as a sampling container.

FIG. 5 shows a system in which samples are taken using bottle 43 placed in sealed container 46 equipped with sight glass 44. To take samples using this configuration, bottle 43 must first be placed in sealed container 46 and connected with bayonet coupling 47 to extraction device 14; after checking that valve 48 in conduit 49 is in the closed position, and after rinsing conduit 1, shown in FIG. 1, with liquid 2 by operating pumping lever 8, stopper 15 is withdrawn, allowing the liquid to flow through opening 17 and fill bottle 43. When the desired level of liquid 45 is reached inside bottle 43, as seen through the sight glass 44, filling may be stopped by pushing the stopper 15 into opening 17. The bottle containing liquid sample 45 may be withdrawn after opening vale 48 to allow the interior of container 46 to return to atmospheric pressure and extract the toxic gases found there.

Modifications and variations of the invention are possible in light of the above teachings. It is therefore to be understood that within the scope of the appended claims, the invention may be practiced otherwise than as specifically described.

What is claimed and desired to be secured by Letters Patent of the United States is:

1. A device for collecting a sample of a liquid contained in a vessel, said device comprising, a conduit having a lower extremity disposed in the vessel, a hollow cylinder having a first end in communication with said lower extremity and a second end spaced from the first end, said cylinder being submerged in the liquid to permit a sample of the liquid to flow into the cylinder, said ends of said cylinder defining the length thereof, the second end of the cylinder having a flared extremity formed thereon, a semi-rigid wire passing through the conduit, a piston connected to a terminal end of the wire and movable reciprocally within the cylinder by actuation of the wire, the piston having a seal to matingly engage the inner wall of the cylinder, the piston being operable by actuation means connected to said wire external of the vessel to move the piston along the length of said cylinder and thereby move the liquid within the cylinder and through the conduit to a sample collection means.

2. A device as claimed in claim 1 wherein the sample collection means includes an inclined extraction tube located at an upper extremity of the conduit extending out of the vessel, the ends of the extraction tube being closed by transparent glass discs.

3. A device as claimed in claim 2 including a conical intersecting opening passage formed in the extraction tube, a stem stopper operable to close said opening passage and a sampling container affixed to the extraction tube adjacent to the opening passage, whereby when the stem stopper is withdrawn from the opening passage, liquid can flow through the opening passage into the sampling container.

4. A device as claimed in claim 2 in which the inclined extraction tube has an opening at the lowest point of the extraction tube, a return conduit connected between said opening and the vessel, whereby liquid in the extraction tube can be returned to the vessel by gravity.

5. A device as claimed in claim 2 including a sampling container connected to the inclined extraction tube by a bayonet coupling.

6. A device as claimed in claim 2 including a sampling container connected to the inclined extraction tube by bayonet pins sealed in a neck portion formed in a wall of the extraction tube.

7. A device as claimed in claim 2 including a sampling bottle retained in a sealed container connected to the inclined extraction tube by a bayonette connector.

8. A device as claimed in claim 7 including a conduit with a valve in communication with the sealed container to evacuate the pressure of gas which accumulates inside and outside of the sampling bottle.

9. A device as claimed in claim 1 in which said actuation means comprise a lever.

10. A device as claimed in claim 1 in which said actuation means comprise a pneumatic jack.

11. A device as claimed in claim 10 including a return conduit for returning liquid to the vessel, a compartment formed in said return conduit, the compartment having a bottom and a side, the compartment including a hole formed in said bottom and an overflow opening in said side, and a sensor in the compartment to measure characteristics of the returned liquid by signals transmitted to a remote indicator.

12. A device as claimed in claim 10 in which the pneumatic jack includes a sealed tube, a pump piston located within the tube and formed of a permanent magnet, said pump piston connected to said wire, and a permanent ring magnet positioned external of the sealed tube and operable to move the pump piston by magnetic force.

* * * * *